United States Patent

Harding et al.

Patent Number: 5,367,378
Date of Patent: Nov. 22, 1994

[54] HIGHLIGHTED PANEL INSPECTION

[75] Inventors: Kevin G. Harding, Ann Arbor; Albert J. Boehnlein, Ypsilanti, both of Mich.

[73] Assignee: Industrial Technology Institute, Ann Arbor, Mich.

[21] Appl. No.: 70,565

[22] Filed: Jun. 1, 1993

[51] Int. Cl.$^5$ .................................... G01B 11/30
[52] U.S. Cl. ................................ 356/371; 356/376
[58] Field of Search ............... 356/371, 373, 376, 374, 356/394, 237, 392, 445, 446, 448; 358/106, 107; 250/561, 562, 571, 572

[56] References Cited

U.S. PATENT DOCUMENTS

| | | | |
|---|---|---|---|
| 2,867,149 | 1/1959 | Goddard | 356/371 |
| 5,237,404 | 8/1993 | Tanaka et al. | 356/376 |
| 5,309,222 | 5/1994 | Kamei et al. | 356/376 |

FOREIGN PATENT DOCUMENTS

| | | | |
|---|---|---|---|
| 0486219 | 5/1992 | European Pat. Off. | 356/371 |
| 0269006 | 11/1988 | Japan | 356/371 |
| 0210807 | 8/1989 | Japan | 356/371 |
| 0285208 | 11/1990 | Japan | 356/371 |

Primary Examiner—Richard A. Rosenberger
Assistant Examiner—Hoa Q. Pham
Attorney, Agent, or Firm—Harness, Dickey & Pierce

[57] ABSTRACT

A method of evaluating defects in a surface as compared with a reference surface by providing a surface for defect evaluation, illuminating and projecting a pattern of lines on the surface having a periodic configuration with features having a separation period, providing a camera for recording a reflected image of the pattern of lines projected and reflected from the surface, and evaluating and quantifying the image by calculating a slope of a defect observed by the camera using a specified relationship. The distance between the illuminated pattern and the surface are used to calculate the defect slope and a defect depth value is generated using a specified relationship dependent on length of a defect area visually recognizable from the reflected image and the calculated defect slope.

2 Claims, 2 Drawing Sheets

HIGHLIGHTED PANEL INSPECTION

BACKGROUND AND SUMMARY OF THE INVENTION

This invention relates to an optical inspection system and particularly to one for evaluating surfaces of large contoured panels through quantitative evaluation of a pattern reflected by the surfaces.

The inspection of sheet metal panels for cars has been approached in a variety of ways. The most commonly used method of inspecting panels for shape errors has been the so-called "highlighting" method. The highlighting method has been used in a subjective manner through the use of skilled inspectors who move around the panels to get just the right reflection off the panel that highlights subtle defects.

The inspection of car panels for shape defects has been a popular and active topic for a number of years. There have been numerous techniques applied to this inspection problem, ranging from radar like measurements to purely visual inspection methods. The problems associated with automating the inspection of body panels has two primary considerations which must be addressed: the quantification of the defects, and the inspection technology to be automated. The general nature of the defects fall into such categories as dents, scratches, waviness, wave edge, hi/lo seam, recoil, metal finish, streamers, and dirt pimples. The current inspections for these features is very subjective in nature.

The most common inspection for dents and lows uses an oil type of "highlighting" fluid to provide a glossy finish similar to that seen on a finished painted car. The glossy finish provided by the highlighting makes the panel appear mirror like, permitting a view of an object beyond the panel to be seem in the reflection off the panel. The inspector typically looks at the edge of colored florescent tubes placed around the panel as reflected from the surface of the panel. If the inspector detects the presence of a "wave" in the edge of the light as he or she moves their head past an area, it is marked as having a dent or "error" in the contour. This is the same type of effect of distortion often seen in older window glass. The surface of the panel is acting as a mirror. The light reflected from the panel is deviated according to the surface slope in accordance with the laws of reflection, creating a distorted image of the light fixture, just as if the inspector was looking at a reflection in a "fun house" mirror.

Actually, the image the inspector sees in the reflection off the highlighted panel is generally always distorted in accordance to the shape of the panel. Therefore, the inspector is looking for some "out of the ordinary" distortion, such as a sudden change in an area expected to be flat. In areas which have sudden contour changes, the inspector may actually be looking for a flat area where the surface is expected to be very curved. Markings, surface finish irregularities or an uneven highlighting fluid application can further complicate this inspection with factors which would be different for a painted surface. Just in this simple example, it is obvious that no one decision is necessarily used to inspect the panel. The final analysis of what features or distortions in the reflected image seen off the panel are important is left up to the inspector.

The car buyer sees a similar effect. Many people become aware of irregular contours on the hood of their car when driving under power lines, by the way the reflection of the lines moves over the hood. Seeing stray dips and deviations in the reflection gives a perceived impression of poor quality. A smooth, geometrically uniform reflection is seen as good quality. Different areas of the car are viewed at different angles, relative to the normal to the surface, making the detection of such defects more or less likely. The reason the angle of view becomes important is the same reason structured light gages are sensitive to angle.

If a straight line of light illuminates the surface of a part, at some angle, and is viewed from some different angle, the line will be seen as deviated from a straight line by the surface contour, into a shape which follows some cross-section through the surface. The sensitivity of the projected line to this effect changes as the sum of the tangent of the illumination and viewing angles, as measured from the average normal to the surface. If the line is viewed along the same path it is projected, no deviation is seen if the surface is diffuse. If a specular (mirror like) reflection is used, then the reflected light is deviated by twice the surface slope to the projected line. The resolving power for the average human eye is about 2 minutes of arc (about 0.6 milliradians) or 1 part in 1700. This means that a surface slope error of 2 minutes of arc on a specular surface would be just resolved by the average human observer. Human perception, however, is most sensitive to changes from the surroundings. Therefore, a dent or flat area seen in one area which has little shape to it may not be perceived in an area of sharp transitions.

Human perception is also an important consideration in scratches or small dirt pimples (small bumps which typically occur when dirt is present in the pressing operation). By the resolution criterion above, we know the average observer can resolve about 0.04 inches (1 millimeter) at about 65 inches (1625 millimeters), or by rule of thumb, a person can resolve about 0.02 inches or 0.5 millimeters at an arm's length distance. This does not mean smaller features cannot be seen. Just as we can see stars in the sky which are too distant to resolve (such as a double star), small features can be detected, but will appear not smaller than the 0.02 inches (0.5 millimeters) nor could we distinguish two scratches below our resolution. As the size of a scratch decreases, the amount of light it scatters decreases as its area. The limited resolution of the human eye further reduces the density of light at a point by spreading it over the resolution spot of the eye, thus reducing the contrast of the defect as seen. This defect detection capability is effectively a measure of the ability to collect visual feature information. Any inspection system should take these factors into account to better compare to what would be seen by the customer.

The quantification of the parameters which affect the perceived quality of the body panel is the first step which must be taken to provide a meaningful panel inspection system. Data based on thresholds that may change with dirt levels, evenness of the oil highlight, or light level fluctuations are subjective in nature and can not be easily calibrated. Therefore, an inspection made in one plant may vary greatly from an inspection done in another plant by such methods.

It would also be desirable to produce a quantitative record of the nature and severity of the defects which could be used for documentation purposes. The range and diversity of the defects creates an interpretation task which is a major undertaking in itself. The intent in this invention is not to address the major task of defect interpretation, but to provide a reliable, quantitative means of characterizing the defects seen by the standard highlighting methods.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE INVENTION

Figure 1:
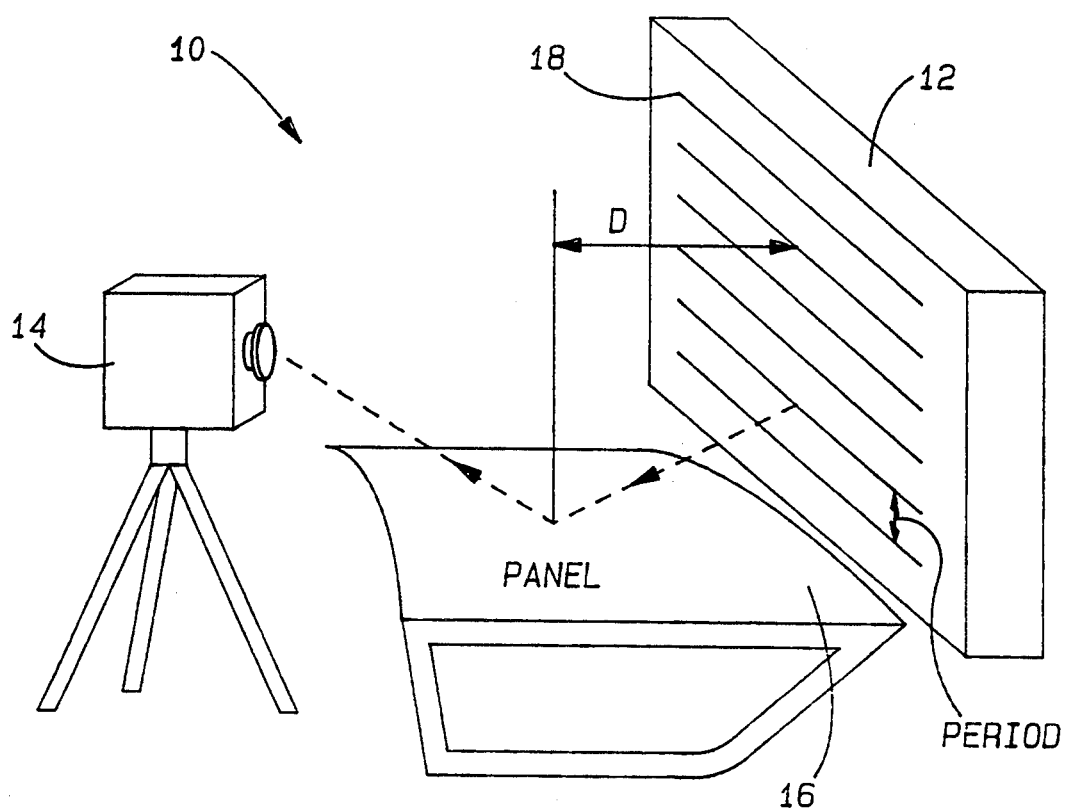
FIG. 1 is a schematic drawing of the panel inspection system of this invention.

With reference to FIG. 1, an inspection system in accordance with this invention is shown and is generally designated by reference number 10. Inspection system 10 generally comprises grid 12 and camera 14, which are shown in the Figure being used for evaluation of a representative panel 16.

Grid 12 is comprised of a "light box" featuring regularly spaced opaque lines 18 which are backlit by a light source (not shown). The separation of the regularly spaced lines 18 defines the period (P) of the grid. As an alternative, a reverse grid could also be used in which opaque lines 18 are instead narrow slits of light.

Lines 18 define a course grid or grating pattern, which are viewed in reflection off panel 16. The use of multiple lines 18 permits the entire panel 16 surface to be inspected from one view, rather than needing to look at the panel from multiple views (to within the limitations discussed later). The lines 18 of grid 12 are deviated as are the lights in the current inspection. The reflected image of grid 12 is photographed by camera 14 from a set view point, producing a two dimensional deviation map over the entire panel. As the grid is being imaged, and not the surface of panel 16, there is not a constant relationship between the deviations seen and the defects on the panel. Therefore, a quantitative value must be obtained for a given deviation which means that each area of an image needs to be calibrated based upon the known geometry of the system.

The interpretation of the data obtained by the highlighted, reflected grid method of this invention must be considered with regard to the actual sensitivity of the highlighting techniques. In viewing a reflection of either a grid or a single light, it is actually the effect that the surface has on the grid line which is seen, not the actual surface shape of the panel itself. The panel surface is simply acting as a mirror. A tilt of a mirror or reflective surface will move the image of what we are looking at by an amplified lever arm between the observer and the mirror, by deviating the line of sight to the subject (the grid line or light). If the mirror simply displaces without tilting, there is a one-to-one effect between the subjects apparent location and the mirror displacement. Therefore, a small change in depth of a thousandth of an inch on the panel will not be even detectable since it is (much less than 0.04 inches or 1 millimeter the eye can resolve at the distance of the grid), but we may still see the change in slope going from a high spot to a low spot, depending on our relationship to the panel.

Referring to FIG. 1, we can calculate the slope angle of the panel 16 surface by measuring how much a grid line 18 has deviated from it's expected course. That is, if we are looking at a flat area, we are looking for how much a line has deviated as a fraction of the period (P) of grid 12, from being a straight line. In the case of a curved area, we must make a judgement as to where the best fit correct curve would be, and how much the observed line has deviated from that curve. This decision may not be too difficult, as we can use the pattern as seen on an acceptable panel as the norm. For one experimental embodiment of this invention given a grating period (P) of 0.20 inches or 5 millimeters, then the effective sensitivity, that is the slope associated with the deviation of a line by one period, would be given by:

$$\text{Slope} = \tan^{-1}(P)/(2D)$$

Where D is the distance shown in FIG. 1 from grid 12 to the location of interest of panel 16 and (P) is the number of periods of the deviation. This is to say, as the distance of the point on panel 16 reflecting the light to grid 12 changes, so does the sensitivity of the measure. We can then calculate the depth change on the panel by:

$$\text{Defect Depth} = (\text{length of defect area})/2 \text{ (Slope)}$$

For the given resolution of the eye of 0.04 inches (1 millimeter), we should be able to see a change of 1/5 of a grid line (i.e. 1/5P). This means that for a defect of 1 inch (25 millimeters) extent (i.e. length of defect area), 24 inches (600 millimeters) from the grid (about the mid-point) designated as dimension D in FIG. 1, we could see a defect related to a change in depth of only 0.0008 inches (about 20 microns). The photographed images could, of course, be enlarged for greater sensitivity than 1/5 (P) grid but as the size of change falls below the resolution limit of the human observer, the 1/5 (P) limit is realistic as a bench mark of noticeable defects.

Determining the distance to the area on the panel that is doing the reflecting is not directly obvious. Photographs from camera 14 actually record an image of grid 12, not of panel 16 per say. In order to determine what area on panel 16 one is looking at, several pictures with locations physically noted by an artifact can be used to construct an overlay to analyze the photos. Because of the "keystone" effect, equal distant points appear closer together at the far end of panel 16 from the viewer or camera 14 than at the near end. In like manner, the sensitivity of inspection system 10 is a function of location on the panel.

The effective sensitivity of inspection system 10 was evaluated using photographs of a set of door panels that were about 4 feet (1.2 meters) in extent. By mapping a set artifact on the panel surface, the inventors found that the effective linear scale as seen from a set perspective at one end of the panel varies by a factor of about 4 over a 4 foot panel placed close to the light, and viewed close to the panel as done by the inspectors. This means that if two defects are seen as the same size (i.e., covering the same area extent on the panel), one near camera 14, and the other near the far end of panel 16, they may in fact be up to 4 times different in extent.

The effective depth sensitivity of the method of this invention, assuming a limited automation of the image analysis to see a change of plus or minus one tenth of a grating period (P) for example, range from 0.0001 inch (2.5 microns) at the end near camera 14, to 0,002 inches (50 microns) at the far end (this is a reasonable sensitivity range for an inspector or the camera to be able to detect). This means the inspector or camera is more sensitive to a defect near him or her, in depth by a factor of 20, and in extent by a factor of 4, than a defect at the other end of the panel. This variation in sensitivity would decrease as the distance from the panel 16 to grid 12 (D) and panel to the inspector or camera 14 increases relative to the size of the panel. That is, if panel 16 were placed about 6 feet (2 meters) from grid 12, a sensitivity variation occurs of about a factor of 2 across a 4 foot (1.2 meter) panel. In fact, the variation in the experimental setup discussed previously is about as much as is possible when defects are positioned very close to each end of the panel. However, such a large variation in sensitivity is not unlike the way the panels are actually inspected.

Figure 2:
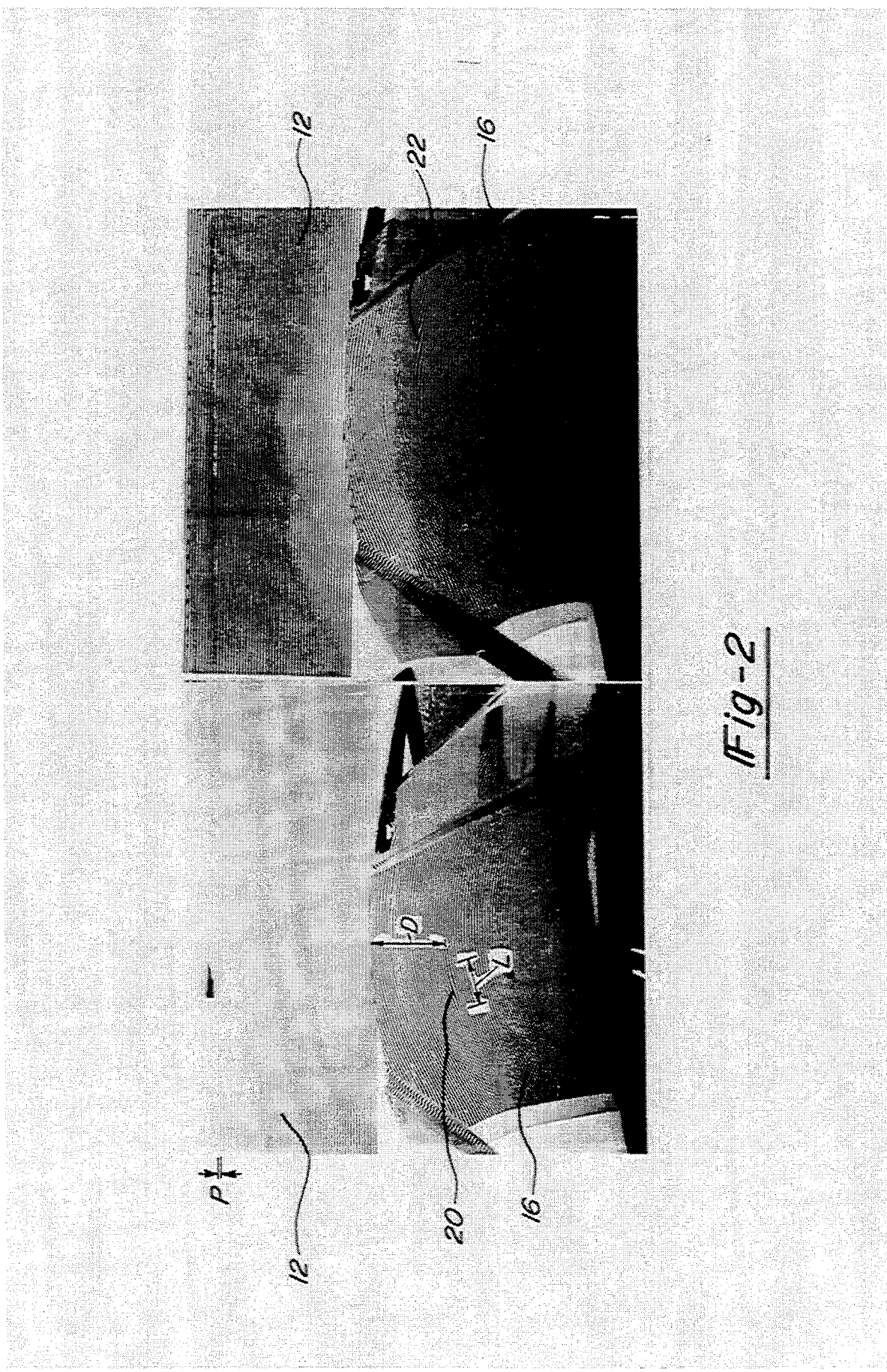
FIG. 2 is a pair of views of a reflected image of a grid from two panels undergoing evaluation in accordance with the method of this invention.

In an evaluation of the method of this invention, a set of four panels (doors) were characterized. Two sample images as seen from a typical inspection location is shown in FIG. 2. The upper part of the image shows the direct view of grid 12 while the lower part shows the deviated grid as seen in reflection off the highlighted panel 16. In each case, one or two small disturbances, for example defect 20 and 22 in the uniformly varying reflected grid image, due to a defect, is clearly visible. Defect 20, which is clearly visible to the unaided eye in the first image of FIG. 2, has a length of defect area (L) whose length is determined by an observer's ability to visually discern deviation between adjacent lines and the reflected grid, and the defect distance from its location on the panel 16 to the grid 12 is denoted as (D).

In evaluating the set of door panels, a range of defects were observed as listed below in Table 1. These defects were considered by an inspector to be typical to severe in some cases (depending on the location).

TABLE 1

| DEFECT SIZE STATISTICS | | | | |
|---|---|---|---|---|
| DEFECT DEPTH | #OF OCCUR- RENCES | OCCURRENCES PER DEFECT WIDTH (INCHES) | | |
| | | <1 | 1–4 | >4 |
| <.0005" | 2 | | 2 | |
| .0005"–.001" | 3 | | 3 | |
| .001"–.0015" | 4 | | 3 | 1 |
| >.0015" | 0 | | | |

Of particular interest in the actual measurements was the very subtle nature of the defects marked on the sample panels. The depth of depression on the lows were in the range of 0.0005 to 0.0015 inches (12 to 36 microns), covering areas of typically about 2 inches (50 millimeters) with some covering as much as 6 inches (150 millimeters). On the larger defects, the wide low or high spots were actually marked by an experienced inspector as two lows or high spots in adjacent areas. This interpretation is not totally unexpected since the line deviations seen in grid reflections off the panels will deviate first going down into a low area, then again coming back up the other side. Some isolated defects marked are actually a single change in panel height, almost like a subtle buckle in the material. The depths of these defects are much less than we had initially expected (thought to be in the few thousandths range), but a separate check with a moire contour measurement system, with measurement capabilities to about 0.0001 inches (2.5 microns) yielded similar numbers for the identified defects.

The results of calibration of this method described above confirms the belief that in order to actually consistently see defects with the same sensitivity over the panel's surface various perspectives of the panel are needed. This same calibration issue, of course, holds true for any such technique that measures a surface based upon the changes it imparts on reflected light, rather than measuring the surface contour itself. A reflection technique such as that of this invention is consistent with what the customer sees. The large variations in sensitivity of an inspection based on reflection can easily make a defect show up clearly from one perspective view, and be invisible from another viewing perspective. This variation in sensitivity could lead to a disagreement in assessing the quality of surfaces such as a panel between the supplier of the panel and the buyer, based upon how the panel is viewed. To be truly a measure of perceived quality, panels or other surfaces should be measured from a set of designed observer locations for that particular type of panel.

While the above description constitutes the preferred embodiments of the present invention, it will be appreciated that the invention is susceptible of modification, variation and change without departing from the proper scope and fair meaning of the accompanying claims.

We claim:

1. A method of evaluating defects in a surface for evaluation as compared with a reference surface, comprising the steps of:

providing said surface for evaluation;

providing illumination means for providing a pattern of lines having a periodic configuration having features having a separation period(P) which can be projected on said surface for evaluation;

providing a camera for recording an image of said pattern of lines as reflected from said surface;

quantifying said image by calculating a slope of a defect observed by said camera using the relationship;

slope=tan$^{-1}$ (Period)/2D where D is the distance between said illumination means and said surface; and generating a defect depth value using the relationship;

Defect Depth=(length of defect area)/2(slope).

2. A method of evaluating defects in a surface for evaluation as compared with a reference surface, comprising the steps of:

providing said surface for evaluation;

providing illumination means for providing a pattern of lines having a periodic configuration having features having a separation period(P) which can be projected on said surface for evaluation;

providing a camera for recording an image of said pattern of lines as reflected from said surface; and quantifying said image by calculating a value of the extent to which said image of said lines as reflected from said surface deviates from an ideal shape of said line wherein said value is scaled in relation to a distance (D) between said illumination means and said surface.

* * * * *